United States Patent [19]

Reif et al.

[11] 4,312,180

[45] Jan. 26, 1982

[54] DETECTING PARTICLES

[75] Inventors: Robert B. Reif, Grove City; Loren R. Albrechtson, Columbus, both of Ohio

[73] Assignee: Battelle Development Corporation, Columbus, Ohio

[21] Appl. No.: 79,866

[22] Filed: Sep. 28, 1979

[51] Int. Cl.$^3$ .............................................. F02C 7/052
[52] U.S. Cl. ................................. 60/39.09 R; 73/28; 73/432 PS; 324/71 CP
[58] Field of Search ......... 324/71 CP; 73/28, 432 PS; 60/39.09 R

[56] References Cited

U.S. PATENT DOCUMENTS

| | | | |
|---|---|---|---|
| 3,114,877 | 12/1963 | Dunham | 324/71 CP |
| 3,679,973 | 7/1972 | Smith et al. | 324/71 CP |
| 3,763,428 | 10/1973 | Preist | 324/71 CP |
| 4,041,768 | 8/1977 | Gibert et al. | 73/28 |

OTHER PUBLICATIONS

Dorman, R. G., "Dust Control and Air Cleaning", Pergamon Press, 1974, pp. 299, 305.

*Primary Examiner*—Robert E. Garrett
*Attorney, Agent, or Firm*—Philip M. Dunson; Barry S. Bissell

[57] ABSTRACT

Apparatus 30 for detecting the presence of more than a negligible concentration of dust or other particles in a moving stream of air or other gas (31), comprising first (1) and second (2) electrically conductive members spaced apart in a first region (A') of the stream (31), means (32) for providing thereto electrical potentials sufficiently different to provide a potential gradient of at least about 30 kilovolts per centimeter in a limited region adjacent to the surface of one of the conductive members (1 or 2), to provide a corona and thus to produce ions that charge a substantial proportion of any particles in the gas (31) passing through the first region (A'); and passive means (33) in a second region (B'') of the stream (31) that is downstream from the first region (A'), for detecting the presence of a detectable concentration of charged particles in the gas (31) while present in the second region (B''). The passive means (33) typically comprises third (3) and fourth (4) electrically conductive members spaced apart in the second region (B''), means (34) for providing thereto electrical potentials of such difference as to provide a potential gradient of substantially less than about 30 kilovolts per centimeter therebetween, and means (35 or 36) for detecting any measurable current flowing to the third member (3) or the fourth member (4).

14 Claims, 3 Drawing Figures

DETECTING PARTICLES

FIELD

This invention relates to methods and apparatus for detecting the presence of more than a negligible concentration of dust or other particles in a moving stream of air or other gas. It is especially useful for protecting engines and other gas receiving devices from damage that would result if the gas entering the device contained too much dust or other particulate matter.

Engines on tanks and other military vehicles require a large supply of clean air to assure maximum engine performance and engine life. Air cleaning systems have been developed that will remove 99 percent of the particulate material that is picked up by the air intake system. Such high efficiency systems are multistage units which include barrier type air filters. However, a simple dust leak in the air cleaning system can negate the effectiveness of the system. The vehicle operator must know when such a leak occurs so that he can shut the engine down and take steps to correct the problem before irreparable damage is done. This problem is especially of concern on military tanks equipped with gas turbine engines that are particularly susceptible to damage by dust in the air under some operating conditions. However, a reliable dust detector system can be valuable on any engine and on many other systems where filters are used to remove dust from the air either to provide a supply of clean air for a particular device or area or to control dust emission from a manufacturing operation or power generation system.

BACKGROUND

Battelle-Columbus Laboratories has conducted extensive research on air filtration systems and especially on electrostatic-assisted systems. In the course of this work, corona-type ionizers have been used to charge air-borne dust, and the charge on airborne dust has been measured and studied in various systems. A relationship was noted between the charge detected in the air downstream from an ionizer and the amount of dust in the airstream, even in relatively clean air.

Electrical coronas commonly are used for charging particles in various types of electrostatic systems for controlling particles in air streams. Coronas produce large numbers of unipolar ions which impart charge to airborne particles by diffusion and bombardment processes. Typically, ion concentrations of $10^7$ to $10^9$ ions per cc can be produced in suitable charging configurations, and the ions have mobilities of about 1.8 to 2.0 cm/sec/volt/cm. These high charge concentrations generally are restricted to the electrical field in the vicinity of the ionizer where the corona is produced.

However, significant charge concentration often can be measured downstream from the ionizers also. Various investigators have noted charge concentrations in outlets from electrostatic precipitators, and certain types of static eliminators produce "charged air". Frequently, this charge is attributed to ions produced by coronas. However, the mobility of gas ions is very high; and, at the usual gas velocities in air cleaners, few if any ions should be blown out of the electrical field where they are generated. For example, if a potential difference of 10 kv is applied between two flat electrodes spaced 1 cm apart, the electrical field strength in the gap between the electrodes is 10 kv/cm. An ion in this field will have a velocity of 2 cm/sec/volt/cm $\times 10 \times 10^3$ volt/cm or $2 \times 10^4$ cm/sec, and the ion will cross the 1 cm gap in $5 \times 10^{-5}$ sec. If the air flow through the gap is 100 fpm or 50 cm/sec, a pair of flat electrodes only $2.5 \times 10^{-3}$ cm long would effectively trap all of the ions generated in the gap.

In U.S. Pat. No. 2,262,370, Penney, dust concentration is measured as a function of the current in an ionizing circuit. This is an active type of detection. Penney's apparatus may include an upstream ionizer to increase the sensitivity, but it is optional. Whether with or without the extra ionizer, Penney's active detection apparatus is much less sensitive than the apparatus of the present invention, wherein the detection is of the passive type.

In accordance with normal usage, an "active" detection circuit is one in which energy is supplied and the condition to be detected can affect the rate of consumption of the energy, while a "passive" detection circuit is one in which the condition to be detected itself furnishes a detectable amount of energy. A typical active detector provides current and measures fluctuations in the current. A typical passive detector operates without current until air flow carries a current of charged particles into the detector.

Typical apparatus according to the present invention for detecting the presence of more than a negligible concentration of dust or other particles in a moving stream of gas comprises first and second electrically conductive members spaced apart in a first region of the stream, means for providing thereto electrical potentials sufficiently different to provide a potential gradient of at least about 30 kilovolts per centimeter in a limited region adjacent to the surface of one of the conductive members, to provide a corona and thus to produce ions that charge a substantial proportion of any particles in the gas passing through the first region; and passive means in a second region of the stream that is downstream from the first region, for detecting the presence of a detectable concentration of charged particles in the gas while present in the second region.

The passive means comprises third and fourth electrically conductive members spaced apart in the second region, means for providing thereto electrical potentials of such difference as to provide a potential gradient of substantially less than about 30 kilovolts per centimeter therebetween, and means for detecting any measurable current flowing to the third or the fourth member. Typically either the third or the fourth conductive member, but not both, comprises an extension of either the first or the second conductive member. Commonly the gas is air.

Typically the first and second conductive members are located substantially coaxially with the stream in the first region. The first conductive member typically comprises a hollow and substantially cylindrical conductor surrounding the sides of the first region and open at both ends, and the second conductive member comprises a relatively thin conductor positioned inside the first conductive member and located approximately along the axis of the first conductive member. The third and fourth conductive members are typically located substantially coaxially with the stream in the second region. Typically the third conductive member comprises a hollow and substantially cylindrical conductor surrounding the sides of the second region and open at both ends, and the fourth conductive member comprises a relatively thin conductor positioned inside the third conductive member and located approximately along the axis of the third conductive member.

Where the first conductive member comprises a hollow and substantially cylindrical conductor surrounding the sides of the first region and open at both ends, the second conductive member comprises a relatively thin conductor located approximately along the axis of the first conductive member, the third conductive member comprises a hollow and substantially cylindrical conductor surrounding the sides of the second region and open at both ends, and the fourth conductive member comprises a relatively thin conductor located approximately along the axis of the third conductive member. The third conductive member typically comprises an extension of the first conductive member. Alternatively, the fourth conductive member may comprise an extension of the second member, in which case the third conductive member is insulated from the first conductive member (and typically from the rest of the flow system).

The apparatus typically comprises also filter means upstream from the first region for removing dust and other particles from the stream of gas, a gas receiving device downstream from the second region, and means such as a servo mechanism responsive to the current detecting means for avoiding damage to the receiving device whenever the current detecting means indicates the presence of a predetermined concentration of charged particles in the second region. Where the gas receiving device is an engine, the current responsive means typically comprises means such as a valve for blocking the flow of gas between the second region and the engine. The current responsive means typically comprises also means for stopping the engine. The current responsive means may comprise also means for providing a warning signal such as a visible or audible alarm.

DRAWINGS

CARRYING OUT THE INVENTION

Figure 1:
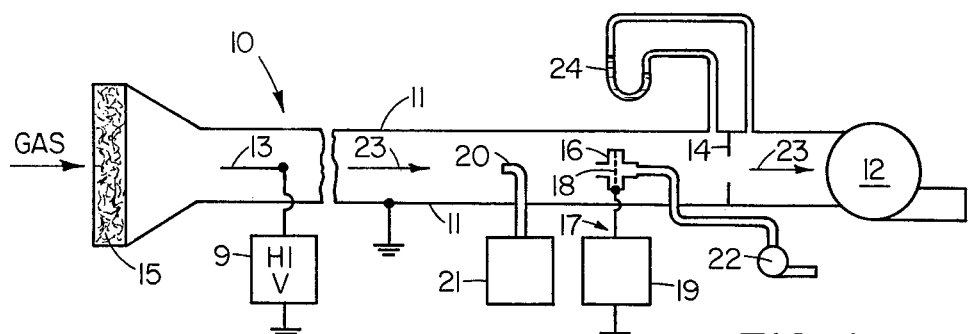
FIG. 1 is a schematic view, partly sectional, of typical apparatus according to the invention.

A simple experiment was conducted at Battelle-Columbus Laboratories which established that fine dust particles are the primary charge carriers in such situations. A test duct 10 (FIG. 1) was set up consisting of a 6-inch-diameter pipe 11 with a blower 12 on the downstream end to pull air through the pipe 11. A charging unit (ionizer) consisting of a 0.004-inch-diameter wire 13 was mounted coaxially in the pipe 11 near the upstream end. A high voltage supply 9 provided the charging potential of about 30 kilovolts to the wire 13. Gas flow was regulated with a flow calibration orifice 14 and variable speed drive on the blower 12. The upstream end of the pipe 11 was fitted with a filter holder to support a filter 15 comprising a 1-foot-square sheet of ½-inch PF105 Fiberglas. A probe 16 from a charge detector 17 consisting of an insulated 0.8-micron-pore silver membrane filter 18 connected to a 600 series Keithley electrometer 19 and a probe 20 from a Dynac SM201A particle counter 21 were inserted into the pipe 11 downstream from the charging wire 13. A vacuum pump 22 controlled the flow rate in the probe 16 of the charge detector 17. The particle counter 21 provided simultaneous readout for four particle size ranges. Particle counts and charge in the gas stream 23 were measured simultaneously as the filter 15 was inserted and removed from the position upstream from the charging wire 13. The gas flow rate was adjusted by the blower 12 to maintain the same flow velocity in the pipe 11 with and without the filter 15 in place. A manometer 24 measured the pressure difference across the flow calibration orifice 14.

Data in Table 1 show that the reduction in charge current in the gas downstream from the ionizer was similar to the reduction in particle concentration produced by placing the filter upstream of the ionizer at gas flow rates of 200 and 1000 fpm. The actual probe current, total particle level, and particle size distribution shifted as the composition of the atmospheric dust changed, but each set of measurements was made over a short time period while the composition of the natural dust was fairly constant.

TABLE 1

| | | | | | | | | |
|---|---|---|---|---|---|---|---|---|
| | | | EFFECT OF PARTICLES ON PROBE CURRENT | | | | | |
| | Ionizer | | Probe | Reduction in Particles, percent | | | | Reduction in |
| Low | Voltage, kV | Current, mA | Current, mA | >0.5 Micron | >1.0 Micron | >3.0 Microns | >5.0 Microns | Probe Current percent |
| 200 | 20 | 0.13 | $6.1 \times 10^{-10}$ | 77.8 | 79.6 | 78.4 | 79.0 | 78.3 |
| 200 | 20 | 0.13 | $9.7 \times 10^{-10}$ | 75.2 | 83.4 | 82.3 | 81.3 | 83.7 |
| 1000 | 20 | 0.13 | $3.3 \times 10^{-10}$ | 89.6 | 91.8 | 92.2 | 92.3 | 96.2 |
| 1000 | 30 | 0.21 | $1.7 \times 10^{-10}$ | 89.5 | 92.4 | 91.5 | 92.3 | 98.1 |

In effect, removing about 80 percent of the atmospheric dust decreased the charge carried in the gas downstream from the ionizer by about 80 percent also at the flow rate of 200 fpm. The higher efficiency at the flow rate of 1000 fpm is attributed to increased inertial effects produced by the higher flow velocity through the filter.

This simple experiment demonstrates that with flow velocities in the range normally used in ionizers in precipitators, most of the charge downstream from the ionizer is carried by fine particles of dust. In the absence of the dust, little if any charge would be expected to be carried out of an ionizer. This system thus provides a simple means for monitoring the presence or absence of dust in an air stream, while at the same time quantitizing the amount of dust.

Figure 2:
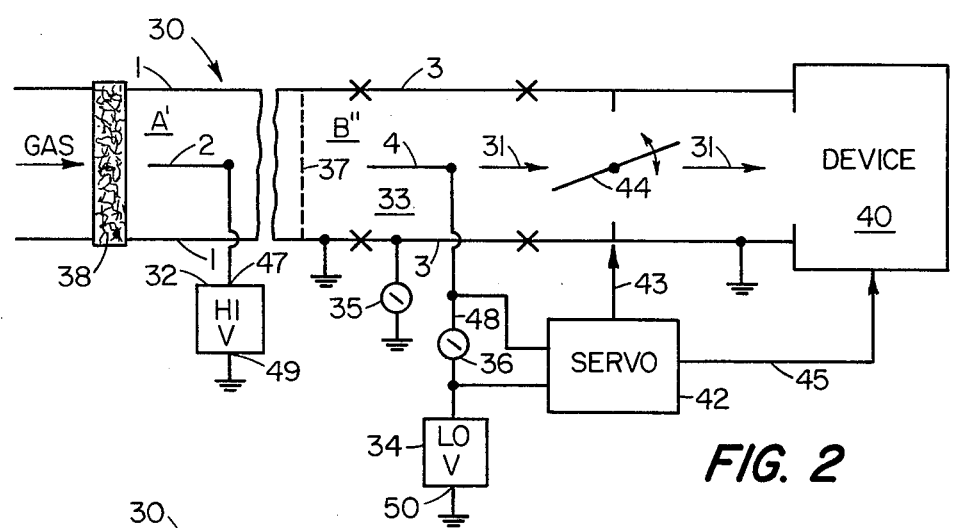
FIG. 2 is a schematic view, partly sectional, of a presently preferred embodiment of the invention.

Referring now to FIG. 2, typical apparatus 30 according to the present invention for detecting the presence of more than a neglibile concentration of dust or other particles in a moving stream of gas 31 comprises first and second electrically conductive members 1 and 2, respectively, spaced apart in a first region A' of the stream 31, means such as a high voltage supply 32 for providing thereto electrical potentials sufficiently different to provide a potential gradient of at least about 30 kilovolts per centimeter in a limited region adjacent to the surface of the conductive member 2, to provide a corona and thus to produce ions that charge a substantial proportion of any particles in the gas 31 passing through the first region A'; and passive means 33 in a second region B" of the stream 31 that is downstream from the first region A', for detecting the presence of a detectable concentration of charged particles in the gas 31 while present in the second region B".

The passive means 33 typically comprises third and fourth electrically conductive members 3 and 4, respectively, spaced apart in the second region B", means such as a low voltage supply 34 for providing thereto electrical potentials of such difference as to provide a potential gradient of substantially less than about 30 kilovolts per centimeter therebetween, and means such as a current measuring electrometer or a microammeter 35 or 36 for detecting any measurable current flowing to the third or the fourth member 3 or 4. Typically either the third conductive member 3 or the fourth conductive member 4, but not both, comprises an extension of either the first conductive member 1 or the second conductive member 2. Commonly the gas is air.

Figure 3:
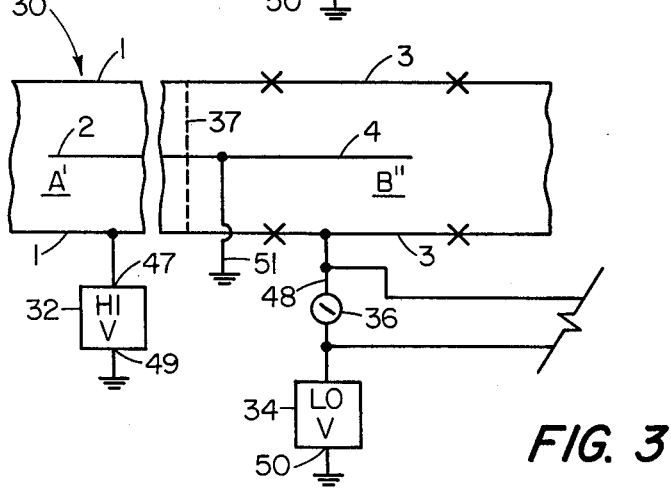
FIG. 3 is a schematic view, partly sectional, of an alternative embodiment for a portion of the preferred embodiment in FIG. 2, including alternative electrical circuitry.

Typically the first and second conductive members 1, 2 are located substantially coaxially with the stream 31 in the first region A'. As in FIG. 2, the first conductive member 1 typically comprises a hollow and substantially cylindrical conductor surrounding the sides of the first region A' and open at both ends, and the second conductive member 2 comprises a relatively thin conductor positioned inside the first conductive member 1 and located approximately along the axis of the first conductive member 1. Also as in FIG. 2, the third and fourth conductive members 3, 4 typically are located substantially coaxially with the stream 31 in the second region B". Typically the third conductive member 3 comprises a hollow and substantially cylindrical conductor surrounding the sides of the second region B" and open at both ends, and the fourth conductive member 4 comprises a relatively thin conductor positioned inside the third conductive member 3 and located approximately along the axis of the third conductive member 3.

Where the first conductive member 1 comprises a hollow and substantially cylindrical conductor surrounding the sides of the first region A' and open at both ends, the second conductive member 2 comprises a relatively thin conductor located approximately along the axis of the first conductive member 1, the third conductive member 3 comprises a hollow and substantially cylindrical conductor surrounding the sides of the second region B" and open at both ends, and the fourth conductive member 4 comprises a relatively thin conductor located approximately along the axis of the third conductive member 3, as in FIG. 2, the third conductive member 3 typically comprises an extension of the first conductive member 1. Alternatively, the fourth conductive member 4 may comprise an extension of the second member 2, in which case the third conductive member 3 is insulated from the first conductive member 1 (and typically from the rest of the flow system) as indicated by the four X marks in FIG. 2 and in FIG. 3. Also the high voltage supply 32, instead of being connected at its upper terminal 47 to the second conductive member 2 (as in FIG. 2), is connected at its terminal 47 to the first conductive member 1, as in FIG. 3. Similarly the upper terminal 48 of the electrometer or microammeter 36 is connected, not to the fourth conductive member 4 (as in FIG. 2), but instead to the third conductive member 3, as in FIG. 3. The second conductive member 2 and its extension (fourth conductive member) 4 are connected to ground (as indicated at 51 in FIG. 3), to complete the circuits for the first region A' and the second region B" to the grounded terminal 49 of the high voltage supply 32 and the grounded terminal 50 of the low voltage supply 34, respectively. (The electrometer or microammeter 35 is of course disconnected from the third conductive member 3 with this alternative circuitry.)

To assure sufficient electrical isolation between the first region A' and the second region B", a grounded screen 37, or a bend or baffles (not shown), may be provided in the flow path between the two regions A' and B".

The apparatus 30 typically comprises also filter means 38 upstream from the first region A' for removing dust and other particles from the stream of gas 31, a gas receiving device 40 downstream from the second region B", and means such as a servo mechanism 42 responsive to the current detecting means 36 for avoiding damage to the receiving device 40 whenever the current detecting means 36 indicates the presence of a predetermined concentration of charged particles in the second region B". Where the gas receiving device 40 is an engine, the current responsive means 42 typically comprises means, as indicated at 43, for controlling a valve 44 or other equivalent means for blocking the flow of gas 31 between the second region B" and the engine 40. The current responsive means 42 typically comprises also means, as indicated at 45, for stopping the engine 40. The current responsive means 42 may comprise also means for providing a warning signal such as a visible or audible alarm.

The active means in the first region A' may consist of other first conductive members 1 such as parallel plates and other second conductive members 2 such as pointed elements, elements with sharp edges, or elements such as saw blades. These elements may be arranged in various configurations as well known in the art for ionizers. Passive means in the second region B" may also consist of two or more equally spaced parallel plates essentially with the same field strength between each pair of plates or with two or more thin walled coaxial cylindrical elements with equal field strength in the annular gap between facing surfaces.

APPLICABILITY

The invention is particularly suitable for use in vehicles equipped with gas turbine engines, such as tanks and trucks. Gas turbine engines are easily damaged by dust and the invention provides a means for assuring that the air filters in such engines are performing satisfactorily. Also, the invention can be used to monitor the exhaust from an internal combustion engine to determine if particulate emissions from the engine exceed an acceptable limit. Similarly, the invention can be used to monitor the particle concentration in any dust control system or in a general working area such as in a textile mill, grain elevator, cement plant, or power generation plant.

The invention is small, rugged, and operates with low power (at most a few watts). It operates much faster and is more sensitive than existing devices which collect a sample of the dust in a filter and measure the pressure drop across the filter. It is more sensitive than the type of active ionizer devices such as the Penny device in which the effect of the particles on a corona current is monitored to determine whether particles are present in the air, and it is more rugged than the light scattering type of particle monitors and densitometer-type smoke meters.

We claim:

1. Apparatus for detecting the presence of more than a negligible concentration of dust or other particles in a moving stream of gas comprising first and second electrically conductive members spaced apart in a first region of the stream, and positioned substantially coaxially with the stream, means for providing thereto electrical potentials sufficiently different to provide a potential gradient of at least about 30 kilovolts per centimeter in a limited region adjacent to the surface of one of the conductive members, to provide a corona and thus to produce ions that charge a substantial proportion of any particles in the gas passing through the first region, and passive means in a second region of the stream that is downstream from the first region, for detecting the presence of a detectable concentration of charged particles in the gas while present in the second region, the passive means comprising third and fourth electrically conductive members spaced apart in the second region, and positioned substantially coaxially with the stream, means for providing thereto electrical potentials of such difference as to provide a potential gradient of substantially less than about 30 kilovolts per centimeter therebetween, and means for detecting any measurable current flowing to the third or the fourth member.

2. Apparatus as in claim 1, wherein either the third or the fourth conductive member, but not both, comprises an extension of either the first or the second conductive member.

3. Apparatus as in claim 1, wherein the gas is air.

4. Apparatus as in claim 1, wherein the first conductive member comprises a hollow and substantially cylindrical conductor surrounding the sides of the first region and open at both ends, and the second conductive member comprises a relatively thin conductor positioned inside the first conductive member.

5. Apparatus as in claim 4, wherein the second conductive member is located approximately along the axis of the first conductive member.

6. Apparatus as in claim 1, wherein the third conductive member comprises a hollow and substantially cylindrical conductor surrounding the sides of the second region and open at both ends, and the fourth conductive member comprises a relatively thin conductor positioned inside the third conductive member.

7. Apparatus as in claim 6, wherein the fourth conductive member is located approximately along the axis of the third conductive member.

8. Apparatus as in claim 1, wherein the first conductive member comprises a hollow and substantially cylindrical conductor surrounding the sides of the first region and open at both ends, the second conductive member comprises a relatively thin conductor located approximately along the axis of the first conductive member, the third conductive member comprises a hollow and substantially cylindrical conductor surrounding the sides of the second region and open at both ends, and the fourth conductive member comprises a relatively thin conductor located approximately along the axis of the third conductive member.

9. Apparatus as in claim 8, wherein the third conductive member comprises an extension of the first conductive member.

10. Apparatus as in claim 8, wherein the fourth conductive member comprises an extension of the second member.

11. Apparatus as in claim 1, comprising also filter means upstream from the first region for removing dust and other particles from the stream of gas, a gas receiving device downstream from the second region, and means responsive to the current detecting means for avoiding damage to the receiving device whenever the current detecting means indicates the presence of a predetermined concentration of charged particles in the second region.

12. Apparatus as in claim 11, wherein the gas receiving device is an engine and the current responsive means comprises means for blocking the flow of gas between the second region and the engine.

13. Apparatus as in claim 12, wherein the current responsive means comprises also means for stopping the engine.

14. Apparatus as in claim 11, wherein the current responsive means comprises also means for providing a warning signal.

* * * * *